United States Patent [19]

Scheben

[11] Patent Number: 4,866,188
[45] Date of Patent: Sep. 12, 1989

[54] SYNTHESIS OF CYCLIC ETHERS

[75] Inventor: John A. Scheben, Erlanger, Ky.

[73] Assignee: National Distillers and Chemical Corporation, New York, N.Y.

[21] Appl. No.: 637,370

[22] Filed: Aug. 3, 1984

[51] Int. Cl.$^4$ .................. C07D 309/08; C07D 307/06
[52] U.S. Cl. ..................................... 549/377; 549/346; 549/356; 549/427; 549/429; 549/479
[58] Field of Search ........................................ 549/377

[56] References Cited

U.S. PATENT DOCUMENTS 3,766,179  10/1973  Snapp, Jr. et al. ................... 549/377

FOREIGN PATENT DOCUMENTS 540278   4/1957  Canada ................................. 549/377
2930144  2/1981  Fed. Rep. of Germany ...... 549/377

OTHER PUBLICATIONS

Chem. Abstracts 57:15102c (1962).
Reppe et al. (Reppe), Justus Liebig's Annalem der Chemie, 596, pp. 80-82 and 109-111 (1955).

Primary Examiner—Nicky Chan
Attorney, Agent, or Firm—Kenneth D. Tremain

[57] ABSTRACT

A process is disclosed for preparing a cyclic ether which comprises cyclodehydrating a polyhydroxy compound of the general formula

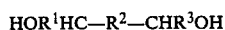

in which $R^1$ and $R^3$, each of which is the same or different, is hydrogen or a lower aliphatic, cycloaliphatic or aryl group and $R^2$ is a divalent aliphatic group of 1 to 10 carbon atoms containing 0, 1 or 2 etheric oxygen atoms or 0, 1 or 2 secondary or tertiary amine nitrogen atoms and 0, 1 or more lower aliphatic, cycloaliphatic and/or aryl groups containing 0 or 1 hydroxyl groups at elevated temperatures in the presence of a catalytically effective amount of a Group VIII metal catalyst or a Group VIII metal-containing material to provide a cyclic ether of the general formula

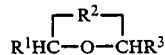

in which $R^1$, $R^2$ and $R^3$ are as defined above. The process is especially useful for preparing the commercially important cyclic ethers tetrahydrofuran and 1,4-dioxane which are derived from 1,4-butanediol and ethylene glycol and/or diethylene glycol, respectively.

20 Claims, No Drawings

SYNTHESIS OF CYCLIC ETHERS

BACKGROUND OF THE INVENTION

This invention relates to the preparation of cyclic ethers such as tetrahydrofuran, furan, tetrahydropyran, 1,4-dioxane, and the like, and more particularly, to the preparation of such cyclic ethers by the catalytic cyclodehydration of a suitable organic starting material possessing at least two hydroxyl groups.

Processes for the cyclodehydration of glycols and glycol ethers to provide cyclic ethers are known. U.S. Pat. No. 2,251,835 describes the cyclodehydration of 1,4-butanediol in the presence of alumina and phosphoric acid catalysts to provide the commercially important cyclic ether tetrahydrofuran. The process described in U.S. Pat. No. 4,007,095 provides 1,4-dioxane, another commercially important cyclic ether, from the cyclodehydration of ethylene glycol or a polyethylene glycol employing an acid catalyst such as sulfuric acid. According to U.S. Pat. No. 4,093,633, tetrahydrofuran is obtained by cyclodehydrating 1,4-butanediol in the presence of an acid catalyst such as sulfuric acid, the product ether being separated from by-product water in a triple column distillation unit. U.S. Pat. No. 4,136,099 discloses the use of tungsten oxide to catalyze the cyclodehydration of 1,4-butanediol to tetrahydrofuran. U.S. Pat. No. 4,196,130 describes he dehydration of diols to cyclic ethers employing aluminum oxide catalyst. U.S. Pat. No. 4,203,908 discloses the dehydration of diols in the liquid phase in the presence of a bleaching earth as the catalyst and of a minor amount of an alkali metal or alkaline earth metal carbonate or bicarbonate. Inoue, et al., *Bull. Chem. Soc. Jpn.*, 53, 3031–3032 (1980) describes the preparation of a variety of saturated and unsaturated cyclic ethers including tetrahydrofuran, tetrahydropyran, tetrahydropyran 2-methanol, 1,4-dioxane, etc., by dehydrating glycol and triol compounds in the presence of an alumina catalyst. Khai, et al., *J. Org. Chem.*, 46, 1759–1760 (1981) describes the cyclization of alpha, omega aliphatic diamines to heterocyclic amines and ammonia employing dichlorotris (triphenylphosphine) ruthenium (II) catalyst complex. No mention is made in this publication of the cyclodehydration of polyhydroxy compounds.

SUMMARY OF THE INVENTION

In accordance with the present invention, a polyhydroxy compound of the general formula $$HOR^1HC-R^2-CHR^3OH$$

in which $R^1$ and $R^3$ each is hydrogen or a lower aliphatic, cycloaliphatic or aryl group containing 0 or 1 hydroxyl groups, $R^2$ is a divalent aliphatic group containing 0, 1 or 2 etheric oxygen atoms, 0, 1 or 2 secondary or tertiary amine nitrogen atoms and 0, 1 or more lower aliphatic, cycloaliphatic and/or aryl substituents depending on the number of carbon atoms present in said group is dehydrated at elevated temperature in the presence of a catalytically effective amount of a Group VIII metal catalyst or a Group VIII metal-containing material to provide a cyclic ether of the general formula

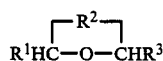

in which $R^1$, $R^2$ and $R^3$ are as defined above.

The process of this invention is particularly useful for the preparation of tetrahydrofuran

which finds industrial use as a solvent for a variety of synthetic resins, notably the polyvinyl resins, in the formulation of topcoating solutions, polymer coating cellophane, protective coatings, adhesives, printing inks, etc., Grignard reactions, lithium aluminum hydride reductions, and polymerizations, and for the preparation of 1,4-dioxane

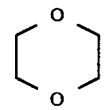

which finds use as a solvent for cellulosics and a wide variety of organic materials, in paints, varnishes, detergents, cosmetics, etc.

DESCRIPTION OF THE PREFERRED EMBODIMENTS

The starting polyols which can be made to undergo dehydration in accordance with this invention to provide cyclic ethers include a wide variety of aliphatic (i.e., saturated and unsaturated) glycols and triols, glycol and triol ethers, glycol and triol secondary and tertiary amines and any of the foregoing containing one or more lower aliphatic, cycloaliphatic and aryl substituents in the aliphatic chain. Specific examples of starting polyols include trimethylene glycol, 1,3-butanediol, 1,4-butanediol, 2,5-hexanediol, 1,6-hexanediol, 1,2,6-hexanetriol, 3-hexene2,5-diol, 1,4-butenediol, ethylene glycol, diethylene glycol, dipropylene glycol, tripropylene glycol, diethanolamine, triethanolamine, dipropanolamine, tripropanolamine, and the like.

A preferred group of polyols for use herein are the alpha, omega diols of the general formula $$HO+CH_2\overline{)_a}(X\overline{)_b}(CH_2\overline{)_a}-OH$$

in which X is oxygen, a is 1 to 4 and b is 0 or 1. This group of diols is inclusive of 1,4-butanediol and diethylene glycol which are especially preferred herein as they provide tetrahydrofuran and 1,4-dioxane, respectively, both cyclic ethers being of considerable industrial importance.

Example of specific starting polyols and the cyclic ethers obtained therefrom in accordance with process of this invention are set forth in the following Table:

TABLE 2

| Starting Polyol | Product Cyclic Ether |
|---|---|
| HO(CH$_2$)$_4$OH |  |
| HO(CH$_2$)$_2$CH(CH$_3$)OH | 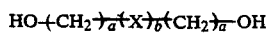 |

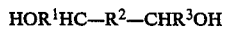

TABLE 2-continued

| Starting Polyol | Product Cyclic Ether |
|---|---|
| HO(CH$_2$)$_2$OH | 1,4-dioxane (6-membered ring with 2 O) |
| HO(CH$_2$)$_2$O(CH$_2$)$_2$OH | 1,4-dioxane (6-membered ring with 2 O) |
| HO(CH$_2$)$_5$OH | tetrahydropyran (6-membered ring with 1 O) |
| HO(CH$_2$)$_3$CH(CH$_3$)OH | 2-methyltetrahydrofuran |
| HO(CH$_3$)CH(CH$_2$)$_2$CH(CH$_3$)OH | 2,5-dimethyltetrahydrofuran |
| HO(CH$_2$)$_6$OH | oxepane (7-membered ring with 1 O) |
| HOCH$_2$CHOH(CH$_2$)$_3$CH$_2$OH | 2-(hydroxymethyl)tetrahydropyran |
| HO(CH$_3$)CHCH=CHCH(CH$_3$)OH | 2,5-dimethyl-2,5-dihydrofuran |
| HO(CH$_2$)$_4$CH(CH$_2$CH$_3$)OH | 2-ethyltetrahydropyran (with CH$_3$) |
| HO(CH$_2$)$_4$CHOH (cyclohexyl) | 2-cyclohexyltetrahydropyran |
| HO(CH$_2$)$_4$CHOH (p-tolyl) | 2-(p-tolyl)tetrahydropyran |

The Group VIII metal catalysts employed in the process of this invention can be in the elemental (zerovalent) state, e.g., ruthenium carbonyl, as a compound such as a ruthenium salt, as a complex, for example, one prepared from a ruthenium salt and carbon monoxide and/or an organic ligand. The salt or complex-containing material can be employed as such or in combination with or deposited upon or affixed to a solid support such as an alumino-silicate zeolite, alumina, silica, zirconia, carbon, and the like. Specific examples of the foregoing include such Group VIII metal salts as nickel, palladium and ruthenium halides, oxides such as platinum and ruthenium oxides, sulfates like ferric sulfate and acetates like palladium acetate and, in particular, the ruthenium halocarbonyls, the ruthenium halides and the ruthenium halocarbonyls in complex association with any of a wide variety of organic ligands. Illustrative of such organic ligands are various piperazines, dipyridyls, N-substituted diamines, aminopyridines, glycolic acid, alkoxy-substituted acetic acids, and the like. Preferred ligands for use herein are phosphine-containing ligands such as trimethylphosphine, triethylphosphine, tri-n-butylphosphine, triamylphosphine, trihexylphosphine, tripropylphosphine, trinonylphosphine, tridecylphosphine, triethylhexylphosphine, di-n-butyloctadecylphosphine, dimethylethylphosphine, diamylethylphosphine, tris(dimethylphenyl)phosphine, ethyl-bis(beta-phenylethyl)phosphine, tricyclopentylphosphine, tricyclohexylphosphine, dimethycyclopentylphosphine, tri-octylphosphine, dicyclohexylmethylphosphine, phenyldiethylphosphine, dicyclohexylphenylphosphine, diphenylmethylphosphine, diphenylbutylphosphine, diphenylbenzylphosphine, trilaurylphosphine and triphenylphosphine. Of the foregoing phosphine ligands, triphenylphosphine is especially preferred.

The catalysts can also be used in combination with a catalyst-promoting amount of an alkali metal halide salt, in particular, the lithium, sodium and potassium iodide, bromide and chloride salts.

Specific examples of catalysts which can be utilized in the practice of this invention are ruthenium metal deposited on carbon, RuO$_2$, RuCl$_3$, [RuCl$_2$(CO)$_3$]$_2$ alone and promoted with lithium bromide and RuCl$_2$(Ph$_3$P)$_3$.

The amount of catalyst, and where employed, catalyst promoter, can vary widely provided, of course, a catalytically effective amount is utilized In general, as little as 0.001 gram atoms of ruthenium per liter of starting polyol are effective to provide reasonable reaction rates with from about 0.002 to about 0.025 gram atoms of ruthenium per liter of polyol being preferred.

Reaction time can vary from as few as 15 minutes to 10 hours or more with good results generally being obtained with reaction times of from 1 to 4 hours.

The cyclodehydration can be carried out in the liquid or vapor phase in a fixed bed or trickle flow catalyst system employing conventional continuous or batch reactor equipment, controls and so forth. Temperatures of from about 150 to about 500° C. and preferably from about 175 to about 300° C. generally provide good results. Pressures from atmospheric to 2,000 psig may also be used. If desired, the dehydration can be carried out in a solvent medium, water being preferred.

Recovery of the cyclic ether is readily accomplished employing known and conventional procedures, e.g., in the case of tetrahydrofuran, the process described in U.S. Pat. No. 4,093,633, and in the case of 1,4-dioxane, the process described in U.S. Pat. No. 4,007,095, both discussed supra, are believed to be suitable.

The following examples are illustrations of the process of the invention:

EXAMPLE 1

The following were added to a 71 ml 316 SS Parr Reactor fitted with a glass liner: dichlorotricarbonylruthenium (II) dimer, [RuCl$_2$(CO)$_3$]$_2$, 0.027 g, 0.107 mmol and 1,4-butanediol, 10 ml, 111.7 mmol. The reactor was sealed and mounted on the arm of a Burrell Shaker. A heated box surrounded the shaker arm. After heating and shaking for one hour at 200° C., the reactor was cooled to room temperature. On opening, 8.9 g of an amber colored liquid was recovered. Gas chromatographic analysis found tetrahydrofuran as the principal reaction product.

Table I contains a listing of the various catalysts and promoters which were tested for activity in the cyclization of 1,4-butanediol to tetrahydrofuran. Examples 2, 3 and 4 demonstrate the effects of temperature and of alumina powder on this reaction. In contrast, Example 5 shows the increased catalytic activity of sulfuric acid, while Examples 6 through 20 demonstrate the high activity of these metal catalysts and promoters.

What is claimed is:

1. A process for preparing a cyclic ether which comprises cyclodehydrating a polyhydroxy compound of the general formula

HOR$^1$HC—R$^2$—CHR$^3$OH in which R$^1$ and R$^3$, each of which is the same or different, is hydrogen or a lower aliphatic, cycloaliphatic or aryl group and R$^2$ is a divalent aliphatic group of 1 to 10 carbon atoms containing 0, 1 or 2 etheric oxygen atoms or 0, 1 or 2 secondary tertiary amine nitrogen atoms, 1 or 2 hydroxyl groups and 0, 1 or more lower aliphatic, cycloaliphatic and/or aryl groups containing 0 or 1 hydroxy groups at elevated temperature in the presence of a catalytically effective amount of a ruthenium metal halide catalyst to provide a cyclic ether of the general formula

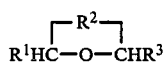

R$^1$HC—O—CHR$^3$

TABLE I

Cyclodehydration of 1,4-Butanediol to Tetrahydrofruan (THF)

| Example | Catalyst | mmol | 1,4-Butanediol mmol | Reaction Time, hr | Reaction Temp. °C. | % THF Yield | Hourly[1] Turnovers |
|---|---|---|---|---|---|---|---|
| 2 | none | — | 111.7 | 1 | 200 | <1 | — |
| 3 | none | — | 61.4 | 2 | 250 | <1 | — |
| 4 | Al$_2$O$_3$ | 3.90 | 113.0 | 2 | 200 | <1 | <1 |
| 5 | H$_2$SO$_4$ | 0.09 | 111.7 | 2 | 165 | 53 | 671 |
| 6 | [RuCl$_2$(CO)$_3$]$_2$ | 0.11 | 61.4 | 2 | 250 | 100 | 1,006 |
| 7 | [RuCl$_2$(CO)$_3$]$_2$ | 0.08 | 111.7 | 2 | 200 | 81 | 2,063 |
| 8 | [RuCl$_2$(CO)$_3$]$_2$ | 0.10 | 111.7 | 1 | 200 | 59 | 2,450 |
| 9 | [RuCl$_2$(CO)$_3$]$_2$ | 0.12 | 111.7 | 2 | 175 | 73 | 1,225 |
| 10 | RuCl$_2$[(C$_6$H$_5$)$_3$P]$_3$ | 0.03 | 111.7 | 2 | 200 | 47 | 11,817 |
| 11 | 5% Ru/Carbon[2] | 0.10 | 111.7 | 2 | 175 | 16 | 564 |
| 12 | RuCl$_3$ | 0.22 | 111.7 | 2 | 165 | 56 | 333 |
| 13 | PdCl$_2$ | 0.30 | 111.7 | 2 | 165 | 46 | 130 |
| 14 | NiCl$_2$ | 0.18 | 111.7 | 3 | 165 | 34 | 127 |
| 15 | Fe$_2$(SO$_4$)$_3$ | 0.19 | 111.7 | 2 | 165 | 61 | 355 |
| 16 | PtO$_2$ | 0.15 | 111.7 | 5 | 200 | 19 | 206 |
| 17 | Pd(OAc)$_2$ | 0.12 | 111.7 | 2 | 200 | 31 | 285 |
| 18 | RuO$_2$ | 0.16 | 111.7 | 2 | 200 | <1 | <1 |
| 19 | RuO$_2$ + LiBr[3] | 0.89 | 111.7 | 2 | 200 | 33 | 88 |
| 20 | [RuCl$_2$(CO)$_3$]$_2$ + SiO$_2$.Al$_2$O$_3$[4] | 0.11 | 111.7 | 2 | 165 | 68 | 1,285 |

[1]Hourly turnovers = hourly mmol of diol converted per mmol of cation charged.
[2]Calculation based on Ru as RuO$_2$.
[3]0.98 mmol.
[4]0.13 g SiO$_2$.Al$_2$O$_3$ zeolite (ZSM-5).

EXAMPLE 21

Hydrated ferric sulfate, 0.10 g (0.186 mmol) was added to an aqueous solution of 1,6-hexanediol, 1,38 g (11.7 mmol) per 5 ml deionized water and the resulting mixture heated and agitated for 2 hours at 200° C. Gas chromatographic analysis of the aqueous layer found hexamethylene oxide, oxepane, at 10% hexanediol conversion. Identity of the product was confirmed by Mass Spectral Analysis.

Similarly, the following glycols were heated with various metal catalysts using the procedures set forth in Example 1.

| Example | Glycol | Catalyst | Product |
|---|---|---|---|
| 22 | Ethylene | [RuCl$_2$(CO)$_3$]$_2$ | 1,4-dioxane |
| 23 | Ethylene | Fe$_2$(SO$_4$)$_3$.nH$_2$O + SiO$_2$.Al$_2$O$_3$[1] | 1,4-dioxane |
| 24 | Diethylene | [RuCl$_2$(CO)$_3$]$_2$ | 1,4-dioxane |

[1]SiO$_2$.Al$_2$O$_3$ = zeolite ZSM-5.

in which R$^1$, R$^2$ and R$^3$ are as defined above.

2. The process of claim 1 wherein the polyhydroxy compound is an alpha, omega diol of the general formula HO—(CH$_2$)$_a$—(X)$_b$—(CH$_2$)$_a$—OH in which X is oxygen, a is 1 to 4 and b is 0 or 1.

3. The process of claim 2 wherein 1,4-butanediol is dehydrated to tetrahydrofuran.

4. The process of claim 2 wherein ethylene glycol and/or diethylene glycol are dehydrated to 1,4-dioxane.

5. The process of claim 1 wherein the ruthenium metal halide catalyst is present on a support.

6. The process of claim 1 wherein the ruthenium metal halide is in complex association with carbon monoxide and/or a ligand.

7. The process of claim 6 wherein the ligand is a phosphine.

8. The process of claim 7 wherein the ligand is a triarylphosphine.

9. The process of claim 8 wherein the ligand is triphenylphosphine.

10. The process of claim 1 wherein a catalyst-promoting amount of an alkali metal halide is present.

11. The process of claim 10 wherein the alkali metal halide is a lithium, sodium or potassium iodide, bromide or chloride.

12. The process of claim I wherein the ruthenium metal halide catalyst is present at a level of at least about 0.001 gram atoms per liter of polyol.

13. The process of claim 12 wherein the ruthenium metal halide catalyst is present at a level of form about 0.002 to about 0.025 gram atoms per liter of polyol.

14. The process of claim 1 carried out at from about 50 to about 500° C.

15. The process of claim 14 carried out at from about 175 to about 300° C.

16. The process of claim 1 carried out at atmospheric to about 2,000 psig.

17. The process of claim 1 carried out in the presence of a solvent.

18. The process of claim 17 wherein the solvent is water.

19. The process of claim 1 wherein said ruthenium catalyst is $[RuCl_2(CO)_3]_2$.

20. The process of claim 1 wherein said ruthenium catalyst is $RuCl_2[(C_6H_5)_3P]_3$.

* * * * *